United States Patent [19]

Woods

[11] 4,353,364

[45] Oct. 12, 1982

[54] EAR ACOUSTICAL ATTENUATING DEVICE

[76] Inventor: Thomas J. Woods, 14124 Dickens St., Sherman Oaks, Calif. 91423

[21] Appl. No.: 138,936

[22] Filed: Apr. 10, 1980

Related U.S. Application Data

[63] Continuation of Ser. No. 870,443, Jan. 18, 1979, abandoned.

[51] Int. Cl.$^3$ ............................................. A61F 11/02
[52] U.S. Cl. .................................................. 128/152
[58] Field of Search ....................... 128/151, 152, 260; 179/1 P; 181/130, 135, 137; D24/67; 2/209

[56] References Cited

U.S. PATENT DOCUMENTS

| Re. 28,560 | 9/1975 | Fling | 128/152 |
|---|---|---|---|
| D. 245,202 | 7/1977 | Asker | 128/151 |
| 2,427,664 | 9/1947 | Dunbar et al. | 128/152 |
| 2,437,490 | 3/1948 | Watson et al. | 128/152 |
| 2,573,923 | 11/1951 | Mezz | 128/152 |
| 2,804,072 | 8/1957 | Genzer | 128/152 |
| 2,888,921 | 6/1959 | Nielson et al. | 128/151 |
| 3,097,643 | 7/1963 | Santi | 128/152 |
| 3,131,241 | 4/1964 | Mendelson | 128/151 |
| 3,565,069 | 3/1969 | Miller | 128/152 |
| 3,871,372 | 3/1975 | Bivins | 128/152 |

FOREIGN PATENT DOCUMENTS 2318735  10/1974  Fed. Rep. of Germany ...... 128/152

Primary Examiner—Henry J. Recla
Attorney, Agent, or Firm—Joseph L. Strabala

[57] ABSTRACT

An ear-insertable protecting device includes a body unit and an integral extending tubular portion adapted to be received in the aperture of the auditory meatus of the ear so it affects a sound seal between the inserted portion and the ear canal with the device having an auditory channel extending therethrough with sound attenuating means located in the auditory channel, includes a cooperating retaining device having a barb at each end which can be plugged into the body unit, in either the auditory channel or another opening provided therefor whereby the device can provide partial or total sound occlusion at the option of the user. In addition, the tubular portion is preferably tapered from the body unit and has a radially extending web wound spirally thereon to facilitate affecting a sound seal with the ear canal without accompanying discomfort. Further, the barb may include a lanyard to prevent loss of the device.

17 Claims, 10 Drawing Figures

U.S. Patent  Oct. 12, 1982  Sheet 1 of 2  4,353,364
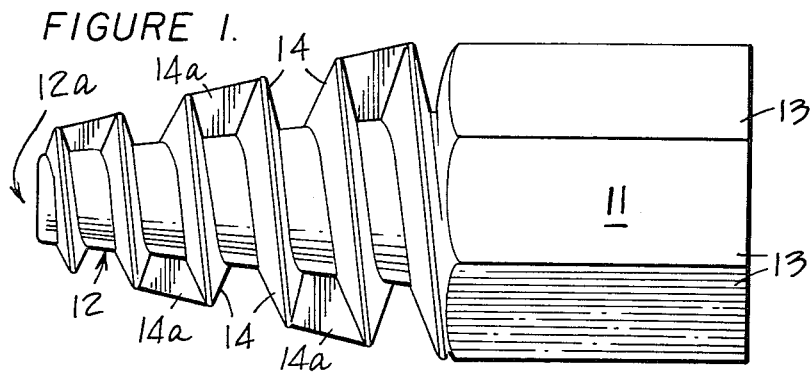
FIGURE 1.
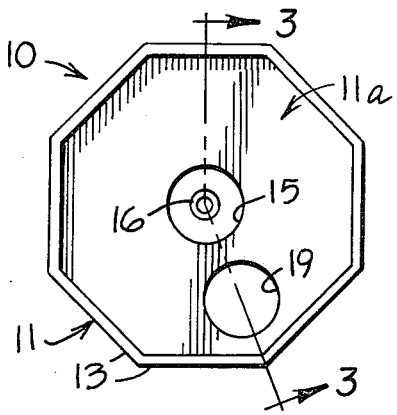
FIGURE 2.
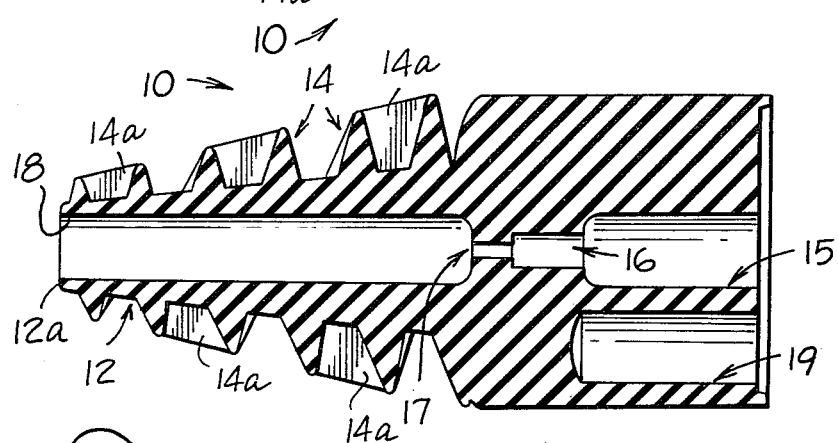
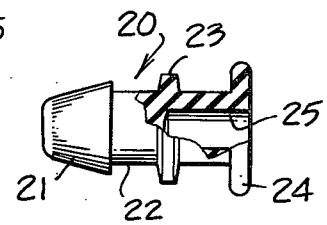
FIGURE 3.
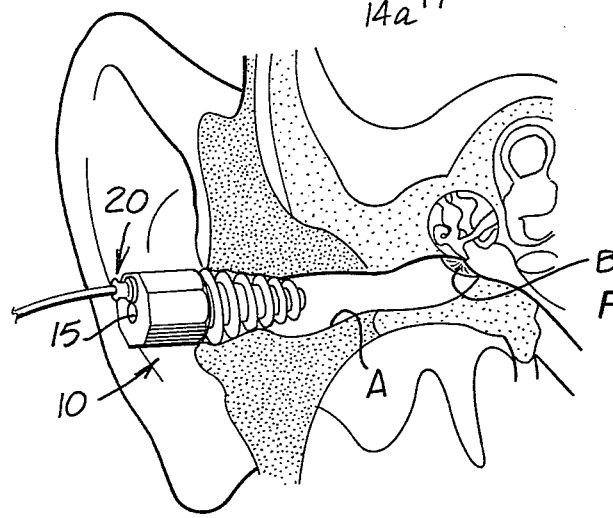
FIGURE 4.
FIGURE 5.
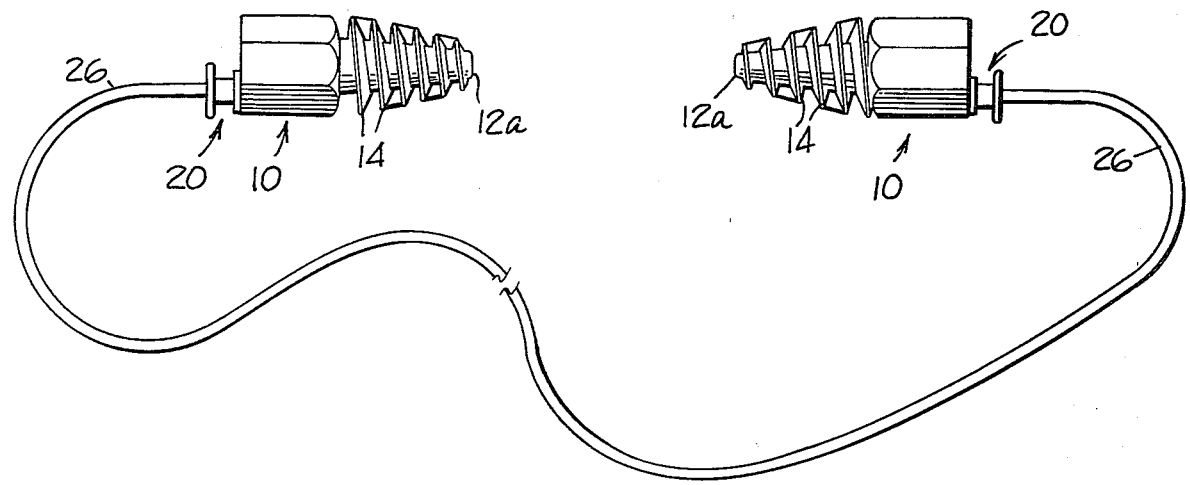

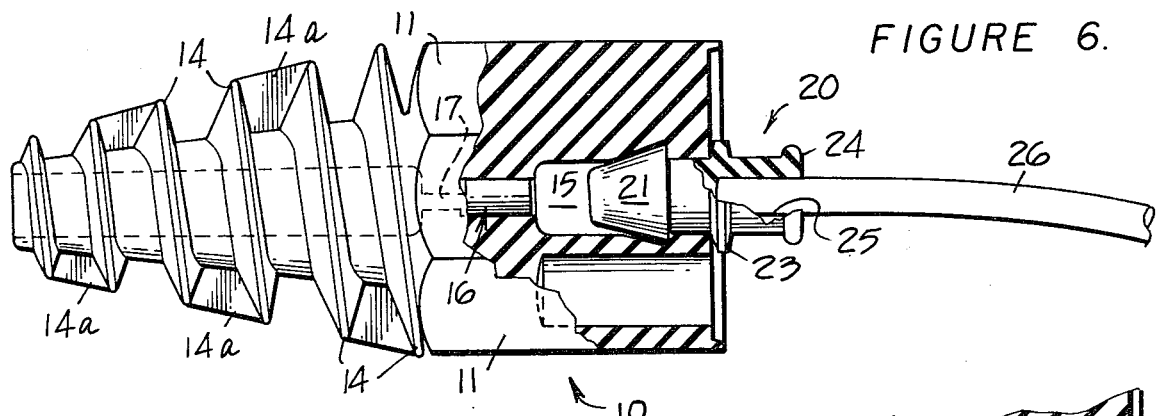
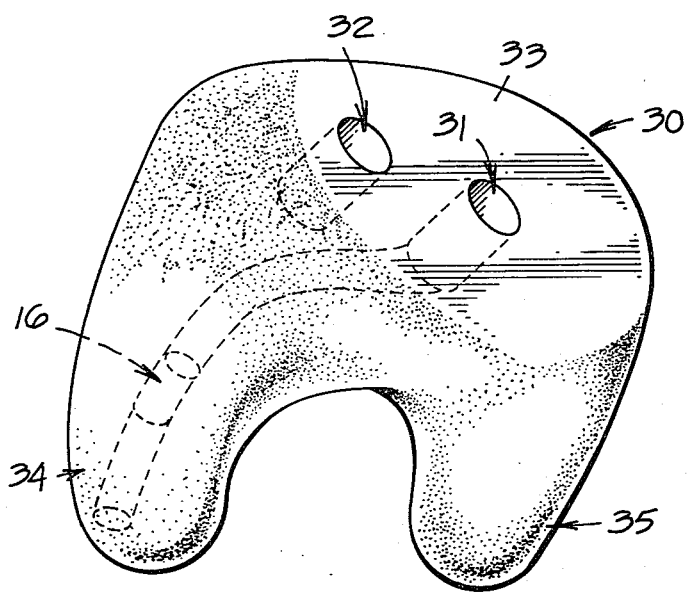
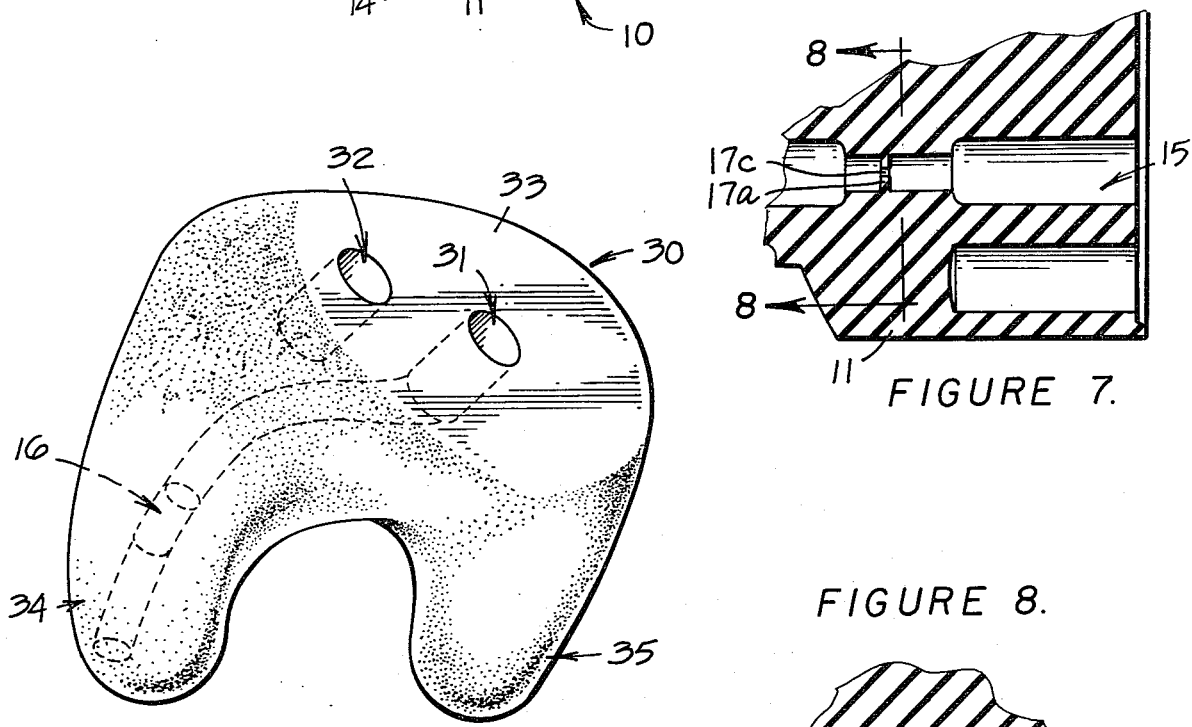
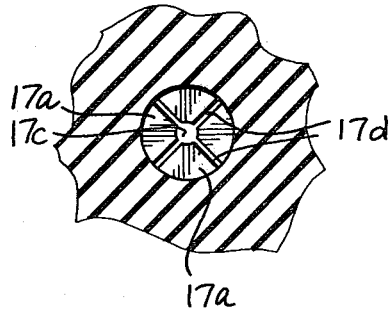

EAR ACOUSTICAL ATTENUATING DEVICE

This is a continuation of Ser. No. 870,443, filed Jan. 18, 1979, now abandoned.

BACKGROUND

Noise levels in our technological society are increasing to dangerous levels and present a real hazard to persons who are required to experience relatively high noise levels over a prolonged period of time. Scientists, doctors and government have become concerned about high noise level intensities in work environments which can ultimately result in a loss of hearing. In 1970, the Federal Government enacted the Occupational Safety and Health Act, having as part of its provisions sections designed to protect millions of industrial workers against the inevitable hearing loss due to the harmful noise level in their working environments.

Close proximity to jet aircraft engines, jackhammers, punch presses, and many industrial processes can subject a person to harmful noise levels of 80 dBA (decibels) and above. If prolonged exposure occurs, loss of hearing will result. For example, California legislation indicates that a person should not be exposed to a sound level of 110 dBA for a period of longer than one-half hour each day.

Many leisure activities may also expose a person to dangerous high sound levels. For example, using equipment such as motorcycles, chain saws, race cars, power lawn mowers and the like can subject an operator of such equipment to harmful noise levels. A snowmobile may have a noise level in the range of 105 dBA and racing motorcycles may reach as high as 110 dBA. Thus, in these situations, it is necessary to take some precautions to prevent loss of hearing. In fact, many pilots have lost their hearing in certain frequency ranges due to the constant and damaging noise levels emitted by piston-type aircraft engines. All sounds having excessively high noise levels of intensity can impair one's hearing, and this includes some of the popular music played on high amplifiers systems at high volumes. Obviously, depending both on the noise amplitude and the frequency, the impairment of one's hearing occurs in the low or high frequencies first. A total loss of hearing can result, depending on the period of exposure to such noise.

Since sound is propagated by pressure waves traveling through the air to one's ears, the hearing loss in many of the above situations can be prevented by wearing protective devices which either partially or totally attenuate these pressure waves. It is quite common for gun enthusiasts to wear ear plugs to attenuate the 140+ dBA impulse sound levels caused by firing a gun.

Regardless of the activity involved for personnel in work environments or in the pursuit of leisure time activities, they are often experiencing dangerously high sound levels and should wear some type of protective device. In fact, in industry, such devices are required by law, and vary from ear-inserted plugs of various kinds to a type of ear muff headgear that is worn over the head, much like ear phones.

The most common type of protective device to prevent loss of hearing in these situations is an ear-inserted plug. Some typical types of ear molds now marketed are shown in U.S. Pat. No. 3,565,069 and U.S. Pat. No. Re. 28,560. In these two patents, a bulbous portion of the ear-insertable mold is received into the auditory meatus (canal) of the ear to hold the mold in place. Obviously, if this bulbous portion does not properly fit the ear canal, sound can by-pass the plug and damage the tympanic membrane (ear drum), regardless of the attenuation provided by the sound-passing channel in the ear mold, if it has one.

With the proper fit, some ear plugs (without a sound passing channel) completely close off the ear canal and prevent any sound from reaching the ear drum except that which is transmitted through the surrounding bone structure. However in ear plugs, it is generally preferred to use devices which vent the ear canal to allow the pressures to equalize within the ear canal with ambient pressure and to pass non-injurious sound waves to the ear drum. This is very desirable since a wearer, where the ear canal is totally occluded by an ear plug, can experience symptoms of vertigo or dizziness, and further, plugs which totally occlude the ear canal are undesirable where a person is experiencing ambient pressure changes, such as when operating an aircraft. For this reason, protective ear devices having a small passage therethrough to allow air pressure equalization are the more preferred type. Also, it is not desirable to prevent a person from hearing sounds totally, since surrounding sounds provide a degree of warning and safety, especially to personnel on production lines. Thus, ideally, an ear-protecting device is one which will pass sound waves of a non-injurious level or intensity while blocking sound levels which can cause damage to the ear drum. U.S. Pat. No. Re. 28,560 attempts to provide such a feature using a membrane to close off the auditory channel in the ear plug when the sound levels passing therethrough exceed a safe level. U.S. Pat. No. 3,565,069 alternatively attempts to achieve the same feature by a resonant filter. Further, any device which reduces the cross-sectional area of the aperture of the ear canal will provide some attenuation of dangerous noise levels, since the sound pressure wave front reaching the ear drum is decreased due to the smaller cross-sectional area of the ear canal with the ear plug in place.

While in most situations it is desirable that the wearer of an ear-protective device be able to hear normal conversation so he can respond to warnings and other stimuli and also use the telephone, there are circumstances where the noise levels become so significant that total occlusion of sound waves in the ear canal is desirable. In view thereof, the most ideal device would be one which the wearer can convert from partial attenuation to total occlusion of sound waves, when the necessity arises. However, to achieve this end, it is still necessary that the portion of the ear-protective device which is inserted into the ear canal fit properly to prevent sound waves from bypassing the device.

The very best sound seal between a device and the ear canal can be obtained with a custom-fitted ear plug which contains a sound channel and sound attenuating device therein. Custom-fitted ear plugs are made by taking an actual impression of each individual ear canal and subsequently casting ear plugs having a perfect fit in the canal. In such a custom-fitted plug a complete sound seal between the ear canal and the device is obtained and the units tend to be quite comfortable when in use. Obviously, the difficulty of custom-fitted ear plugs is that they are costly to produce and can be used by only a single individual for whom they are made. This is true since each person's ear canals are as different as are his fingerprints.

An alternative to the custom-fitted ear plug is a universal device made in several sizes and having on a portion thereof inserted into the ear canal means for effecting a complete sound seal without creating discomfort. Obviously if the ear-protective device is ill-fitting, it will easily dislodge from the ear and become lost, and further, if such devices are uncomfortable, workers will resist wearing them or conveniently lose them in situations where they should be worn for their own protection.

OBJECT OF THE INVENTION

An object of this invention is to provide a universal ear plug which has an improved structure to better fit the ear canal of the wearer.

Another object of this invention is the provision of a convertible ear plug which can provide either total or partial attenuation of sound waves at the election of the wearer.

Still another object is the provision of a removable retention device for ear-protective devices which prevents their loss and serves the double function of converting the device to one having total sound occlusion, if desired.

Other objects and advantages will be apparent from the description of the invention herein and the drawings appended hereto.

SUMMARY OF THE INVENTION

An ear-protective device which can accomplish the objects herein includes a body unit and integral extending tubular portion adapted to be received in the aperture of the auditory meatus of the ear so that it forms a comfortable sound seal between the portion and the ear canal, which device has an auditory channel extending through both the body unit and tubular portion with a sound-attenuating means located in the channel and a separate bore approximately the diameter of the auditory channel cooperating with a barb or plug which can be inserted into the auditory channel or the separate bore at the option of the wearer so that the unit can provide either total sound occlusion or partial attenuation. The barb or plug is preferably part of a retaining device which typically includes a flexible vinyl rod connected between two barbs or plugs forming a loop or lanyard therebetween whereby when the barbs or plugs are inserted into the ear-protective devices on opposite sides of the head, they will provide a device whereby if the plug is dislodged, it will not be lost. In addition, the tubular portion of the device which is inserted into the ear canal is preferably tapered and has a spiral radial web of flexible material extending therefrom whereby the flexible web can comfortably conform with the auditory meatus when the device is inserted into the ear canal.

BRIEF DESCRIPTION OF THE DRAWINGS

FIG. 1 is an elevation of the ear-protective device of the invention showing generally its outer configuration;

FIG. 2 is an end view of the device shown in FIG. 1 illustrating the central auditory channel and the offset separate bore in which means the barb or plug can be inserted at the option of the wearer;

FIG. 3 is a cross-section along line 3—3 of the device showing FIG. 2 with the barb or plug having parts broken away to show its detail;

FIG. 4 is an elevation of the ear-protecting device shown in its environmental application inserted in the auditory meatus (ear canal of the human ear);

FIG. 5 is an elevation of a pair of the ear-protecting devices connected by a lanyard interconnecting the barb or plugs, thereby providing a retaining device when the barbs or plugs are inserted into the apertures of the devices, as shown;

FIG. 6 is an elevation of one of the ear-protecting devices of this invention with the barb or plug inserted in the auditory channel as opposed to the separate bore as illustrated in FIG. 5;

FIG. 7 is a broken away cross-section of an alternate embodiment of the device shown in FIG. 6 in which an integral sound attenuating means is employed;

FIG. 8 is a broken away portion of the integral sound attenuating means shown in FIG. 7;

FIG. 9 is a perspective of a custom-fitted ear-protecting device having an auditory channel and a blind bore together with a barb or plug which can be inserted in either aperture to provide the wearer with partial or total sound occlusion, as he selects;

FIG. 10 is a cross-section of a custom-fitted device shown in FIG. 9 with the barb or plug forming part of the retaining device.

DETAILED DESCRIPTION OF THE PREFERRED EMBODIMENTS

In FIG. 1, the exterior configuration of the ear-protecting device 10 is apparent and its principal components, as shown, are body unit 11 and an integral tubular portion 12 extending therefrom. Cylindrical in shape, the body unit has a length about equal to its diameter and is preferably faceted with outer flat surfaces 13 resulting in an octagonal end configuration, as can be seen in FIG. 2. This faceted exterior is preferable since it makes it more convenient to rotate the device with the fingers when it is inserted into the ear canal as hereinafter described. Made integrally with the body unit 11 is the extending tubular portion 12 which preferably tapers from its connection to the body unit to its distal end 12a. As can be seen in FIGS. 1 and 3, this tubular portion has a radially extending web 14 which spirals along this portion from the body unit to its distal end with the height of the web diminishing progressively along its convolutions as it approaches the distal end of this portion.

In the embodiment of the ear-protecting device shown in the drawings in FIGS. 1–6, the body unit 11 and the tubular portion 12 are axially aligned, whereby a central auditory channel 15 can extend from the outer face 11a of the body unit to the distal end 12a of the tubular portion. This auditory channel 15 provides a passage through which the sound waves can be transmitted from the environmental into the ear canal and subsequently to the ear drum. In order to provide the desirable attenuation within this auditory channel, a sound attenuating means 16 may be utilized in the channel. For example, the acoustical filter described in U.S. Pat. No. 3,565,069 can be inserted into this channel to provide the desired sound attenuation.

If a separate acoustical filter is not used, a sound attenuating means can be integrally formed in the auditory channel 15 by using a series of successively smaller diameters in this channel and controlling the size of aperture 17. Usually the smallest diameter should be in the range of 0.010 to 0.020 of an inch.

As can be seen in FIG. 7, the auditory channel in the embodiment has a reduced diameter in its central portion. In the area of the reduced diameter a diaphragm 17a (best shown in FIG. 8) is employed to close the channel with the exception of the small central aperture 17c on the order of 0.010 to 0.020 of an inch which is centrally formed in the diaphragm. Also, if desired, the diaphragm may include slits 17d from its aperture radially toward its connection to the channel 15 to allow it to pass additional portions of sound waves entering the channel with partial attenuation. This particular structure is highly functional, since a pipe cleaner or some similar device can be passed through the auditory channel 15 to clean any ear wax or foreign material that might lodge in this channel during use. Obviously, the slits allow the cleaner to pass through without damage to the diaphragm, which "reforms" once the cleaner is removed. As a result, maintenance of the device is easy, requiring no special tools or equipment. Of course, the sequential decreasing diameters in this channel also help provide the desired sound attenuation for the protection of the user of device.

Normally, when the integral sound attenuating means is used, the unit 10 is molded using core pins to form the auditory channel 15 and the aperture 17c is subsequently punched in the diaphragm 17a. This diaphragm 17a is usually a membrane with a thickness of about 0.010 inch and aperture 17c can be varied in size to obtain the desirable characteristics.

At the distal end 12a of the tubular portion 12 of the unit, a small spherical indentation 18 is formed to prevent the aperture 17 from becoming occluded with ear wax or the like and to provide additional flexibility to conform to the ear canal.

In the body unit 11 and off the central axis of the device 10, a blind bore 19 is formed in the end 11a. This blind bore is designed to have the same diameter as the auditory channel 15 along a central axis of the body unit. Because of the common diameter of these two apertures, a barb or plug 20 can be inserted into either aperture at the option of the wearer. The barb or plug is somewhat oversized with a bell-shaped head 21 which slightly deforms the elastomer material from which the device is constructed when it is inserted into either aperture, thereby causing it to become securely anchored in either aperture when it is so inserted.

Besides the bell-shaped head 21, the barb or plug 20 includes a tubular shaft 22 extending therefrom which has at spaced-apart locations thereon two radially extending flanges 23 and 24. The latter flange is located at the end opposite the bell-shaped head, and flange 23 is centrally disposed in the tubular body. In addition, the end of the barb opposite the bell-shaped head includes a bore 25 which can receive an end of the flexible vinyl rod 26 by gluing it therein or otherwise effecting a connection therebetween. When the barb or plug is inserted into the auditory channel 15 or the blind bore 19, flange 23 limits its traveling into these apertures, and flange 24 provides a convenient gripping surface to enable one to extract the barb or plug from either of the two apertures so that it can be inserted in the other.

As can be seen in FIG. 5, the flexible rod 26 can be connected to two of the barbs or plugs 20 by attaching its opposite ends in separate plugs or barbs. When this is done, the flexible rod 26 forms a flexible lanyard between the several barbs or plugs, and when the latter are inserted into the ear-protecting device of this invention on opposite sides of the wearer's head, they will form a convenient retaining device to prevent the loss of an ear plug, should it inadvertently become dislodged, or alternatively, be removed by the wearer for some temporary purpose.

Of course, as can be seen in FIG. 6, the barb or plug 20 can be inserted into the auditory channel 15 of the unit shown in FIGS. 1 through 7, whereby the auditory channel is completely occluded. Total sound occlusion is effected except for those vibrations which are transmitted to the bone structure of the skull.

In FIG. 4, the device is shown inserted into the meatus or ear canal A of the human ear. In this position, it will restrict or attenuate sound waves from passing through the ear canal to the tympanic membrane or ear drum B. While bells and discs of differing sizes have been used in the past on the portion of the ear plugs inserted into the aperture of the ear canal and partially therein, they have been generally unsatisfactory due to the irregularities of this canal. By contrast, the instant device is inserted with a twisting motion which will cause the flexible web spiralling down the tapered tubular portion 12 to "work slightly" to effect the necessary seal because tubular portion 12 can deflect and the spiral flexible web 14 forms a thin wall engaging the auditory meatus, the device can be used without causing discomfort. A good sound seal device conforms to the various shapes of individual ear canals. Obviously the web portions must be flexible, and these ear plugs are normally fabricated from elastomers such as "soft" polyvinyl chloride or similar materials which allow the web to be sufficiently flexible to conform to the ear canal. Usually the average thickness of the radially extending web is approximately 0.005 to 0.020 inches, enabling it to deflect as the device is twisted into the ear and oriented to provide the desirable sound seal between the canal and the device. Further, since these webs are sufficiently flexible, they do not cause relatively concentrated pressures against the peripheral surface of the ear canal that cause discomfort to the wearer of the ear plug, which is another desirable feature of this invention. In addition, thinner cross-webs 14a can be included in the spiral as a blocking membrane so that the sound seal can be further improved.

The cross webs 14a are thin membranes which extend between the upstanding portions of the spiral flexible web and prevent a continuous channel from forming along the spiral and within the confines of the peripheral edges of the spiral web. This arrangement insures that sound cannot pass spirally down the channel formed by the spiral web when it is inserted in the human ear.

It should be appreciated that the disposition of the web 14 in the device 10 shown inserted in the ear canal of the human ear in FIG. 4 is for purposes of illustration only, and it is to be recognized that the web will be considerably deflected and deformed in relation to the irregularities of the ear canal in which the unit is installed in actual service. Further, the taper of the tubular portion 12 allows it to fit the different sized apertures of the ear canal in different people. However, still it is desirable that the unit have several sizes available, due to the relatively large variation in the size of the ear canal in various individuals.

Normally the device according to this invention would be cast from what is known as the "soft" vinyls which are non-toxic and non-allergic materials currently available in the marketplace. For instance, an F.D.A. approved vinyl having approximately 50 shore would be entirely suitable for the manufacture of the device according to this invention.

A custom molded ear protecting device 30 is shown in FIGS. 9 and 10 and has a central auditory channel 31 with a blind bore 32 which would allow the barb or plug 20 as shown in FIG. 3 to be utilized with this custom fitted device. As can be seen in the drawings the custom molded device has a main body 33 which conforms to the concha (bowl of the ear), the appendage 34 extending outward from the underside of the bowl fits into the meatus (ear canal) to seal the auditory canal, the other appendage 35 fits in back of the helix of the ear and helps to retain the device comfortably yet firmly in place. These appendages are formed by an impression taken of the ear canal and bowl of the outer ear. The resulting custom molded device is thus retained in the ear by the appendage 34 in the ear canal, and other appendage 35 lodged comfortably behind the helix cavity and the main portion of the single piece mold behind the tragus.

As can be appreciated from the above description, the barbs or plugs 20 can be utilized to convert an ear-protecting device having partial sound attenuation to one having full sound occlusion through the ear canal, if desired. In addition, these barbs or plugs, when connected with the accompanying flexible vinyl rod 26, provide a retention device which eliminates inadvertent loss of these important safety devices. Obviously in the case of the custom-fitted ear plugs, it is highly desirable to utilize the retention device, since the cost of the device is high, and the loss of even a single unit could require the expensive procedures of taking a second impression and molding a replacement ear-protective device.

As explained above, the several devices described are designed to provide a good sound seal between the ear canal and the ear-protecting device. In addition, each has the ability to convert from a partially-attenuating device to a device which fully occludes all sound waves from the ear canal. In fact, these devices have proven quite satisfactory for other uses in the fully occluded configuration such as use for sleeping and for swim plugs, where it is desirable to keep water out of the ear canal for various reasons.

Having described my invention, I claim:

1. An ear hearing protective device comprising:
    an elastomer body means having a first aperture and a second aperture, said first and second apertures being laterally spaced apart and a connecting tubular means extending from said first and second apertures, said tubular means being tapered and adapted to be received in the ear canal of the human ear in a sound-sealing relationship;
    an auditory channel for passing sound waves therethrough extending through said body means from said first aperture therein and through said tubular means to an opening at its distal end;
    a sound attenuating means located in said channel operable to attenuate sound waves, said sound attenuating means having an opening of a lesser diameter than the said channel; and
    a removable plug means selectively inserted in said first aperture communicating with said auditory channel in said body means or in said second aperture therein to provide the wearer with selective total sound occlusion and partial sound attenuating depending upon the position of said plug means in said apertures.

2. The device as defined in claim 1 wherein the plug means includes a flexible cord means having one end thereof connected in said plug means and means on said opposite end adapted to be anchored to a wearer whereby said flexible cord means is operable when the plug means is inserted in one of said apertures in the body means to retain the ear hearing protective device when the other end of the cord means is anchored.

3. The device as defined in claim 2 including a second hearing protective device as defined in claim 1 and wherein said anchoring means comprises a second removable plug means connected to said flexible cord means at its opposite end selectively inserted in said first or second aperture of said second hearing protective device thereby providing a connecting means for said pair of hearing protective devices when the several plug means are inserted in said respective apertures in said respective devices.

4. The device as defined in claim 1 wherein the tubular means includes a radially-projecting continuous web means extending spirally along its length, said web means being flexible, allowing it to deflect to the configuration of the ear canal when it is inserted into the human ear and rotated whereby it is operable to cause said web means to locate in the ear channel in sound sealing relationship as a result of the spiral configuration and rotation.

5. The device as defined in claim 4 wherein the body means has an irregular outer surface to facilitate rotating the tubular means when rotated with the fingers for inserting it into the ear canal of the human ear in a sound-sealing relationship.

6. The ear hearing protective device as defined in claim 1 wherein the sound attenuating means includes a diaphragm disposed transversely in the auditory channel in its central portion which has a plurality of radial slits extending from its center to its circular periphery operable to allow its resulting segmented portions to be displaced by pressure variations caused by sound waves.

7. The hearing protective device as defined in claim 1 wherein the sound attenuating means includes a diaphragm across the auditory channel which has a central aperture from 0.010 to 0.020 inches and a diaphragm thickness of about 0.010 inches.

8. An ear hearing protective device comprising:
    an elastomer body means with a connecting tubular means adapted to be received in the ear canal of a human ear in sound-sealing relationship;
    said tubular means having a radially projecting web means extending spirally along its length, said web means being flexible, allowing it to deflect to the configuration of the ear canal when it is inserted into a human ear and rotated whereby it is operable to cause said web means to locate in the ear channel in a sound-sealing relationship;
    an auditory channel passing axially through said body means and said tubular means operable to pass sound waves therethrough, from a surface on the said body means to the distal end of said tubular means; and
    a sound attenuating means located in said channel operable to attenuate sound waves, said sound attenuating means including a diaphragm across said auditory channel, said diaphragm having a plurality of slits extending from its center to its circular periphery operable to allow the resulting segmented portions to be temporarily displaced by pressures originating from sound waves.

9. The device as defined in claim 8 wherein the tubular means is formed of a tapered member with the spiral web means projecting therefrom.

10. The device as defined in claim 8 wherein the radially projecting web means extending spirally along said tubular means progressively decreases in diameter in its convolutions from the body means to the distal end of said tubular means.

11. The device defined in claim 8 wherein thin membrane means extend between the projecting web means at random locations operable to block a continuous spiral path between said projecting web means at a plurality of locations along said tubular means.

12. The device as defined in clam 8 wherein the body or said means includes a second aperture and a removable plug means which is operably securable in the auditory channel or said second aperture therein.

13. The device as defined in claim 12 wherein the removable plug means includes a flexible cord means whereby the device may be secured to the wearer's person when the plug means is operably received in the auditory channel or said second aperture in said device.

14. An ear hearing protective device comprising an elastomer body having a first aperture and a second aperture laterally spaced from said first aperture and having a connecting tubular means extending from said first and second apertures, said last-named means adapted to be received in the ear canal of a human ear in a sound-sealing relationship;

an auditory channel for passing pressure waves representing sound therethrough extending through said body means from said first aperture thereon and through said tubular means to an opening at the distal end of said tubular means;

sound attenuating means located in said auditory channel operable to attenuate said pressure waves, said sound attenuating means including a diaphragm disposed transversely across said auditory channel, said diaphragm having a plurality of slits extending from its center to its circular periphery operable to allow the resulting segmented portions to be displaced by pressures originating from sound waves; and a removable plug means selectively inserted in said first aperture communicating with said auditory channel in said body means or in said second aperture therein to provide the wearer with selective total sound occlusion and partial sound attenuating depending upon the position of said plug means in said apertures.

15. The ear hearing protective device as defined in claim 14 wherein the tubular means is conically shaped, progressively decreasing in diameter to its distal end, and includes a radially-projected web means extending spirally along its length, said web means being flexible to allow deflection to effect a sound-sealing relationship when the tubular means is received in an ear channel, said web means including a plurality of membrane means extending normally between the convolutions of the spiral thereof at random locations operable to block a continuous spiral path along said tubular means.

16. The ear hearing protective device as defined in claim 14 wherein the diaphragm has a thickness of about 0.010 inches.

17. The ear hearing protective device as defined in claim 14 wherein the diaphragm has a central aperture of a diameter from 0.010 to 0.020 inches.

* * * * *